US011453598B2

(12) United States Patent
Shao et al.

(10) Patent No.: US 11,453,598 B2
(45) Date of Patent: Sep. 27, 2022

(54) SURFACE MODIFIED PIGMENT

(71) Applicants: COLGATE-PALMOLIVE COMPANY, New York, NY (US); KOBO PRODUCTS, INC., South Plainfield, NJ (US)

(72) Inventors: Yun Shao, Belle Mead, NJ (US); David Schlossman, Short Hills, NJ (US); Neringa Kontrimiene, Somerset, NJ (US); Ariel Haskel, East Brunswick, NJ (US)

(73) Assignees: COLGATE-PALMOLIVE COMPANY, New York, NY (US); KOBO PRODUCTS. INC., South Plainfield, NJ (US)

( * ) Notice: Subject to any disclaimer, the term of this patent is extended or adjusted under 35 U.S.C. 154(b) by 77 days.

(21) Appl. No.: 16/584,603

(22) Filed: Sep. 26, 2019

(65) Prior Publication Data
US 2020/0087161 A1 Mar. 19, 2020

Related U.S. Application Data

(63) Continuation of application No. 13/391,594, filed as application No. PCT/US2009/055513 on Aug. 31, 2009, now abandoned.

(51) Int. Cl.
*C01G 23/047* (2006.01)
*A61K 8/29* (2006.01)
*C09C 1/40* (2006.01)
*C09C 1/04* (2006.01)
*C09C 3/10* (2006.01)
*A61K 8/02* (2006.01)
*B82Y 30/00* (2011.01)
*C09C 1/30* (2006.01)
*A61K 8/26* (2006.01)
*C09C 1/36* (2006.01)
*A61Q 19/10* (2006.01)
*C09C 1/24* (2006.01)
*C09C 3/00* (2006.01)
*C09C 1/02* (2006.01)

(52) U.S. Cl.
CPC .......... *C01G 23/047* (2013.01); *A61K 8/0241* (2013.01); *A61K 8/26* (2013.01); *A61K 8/29* (2013.01); *A61Q 19/10* (2013.01); *B82Y 30/00* (2013.01); *C09C 1/021* (2013.01); *C09C 1/043* (2013.01); *C09C 1/24* (2013.01); *C09C 1/3072* (2013.01); *C09C 1/3669* (2013.01); *C09C 1/3676* (2013.01); *C09C 1/402* (2013.01); *C09C 1/405* (2013.01); *C09C 3/006* (2013.01); *C09C 3/10* (2013.01); *A61K 2800/412* (2013.01); *A61K 2800/43* (2013.01); *A61K 2800/63* (2013.01); *C01P 2004/64* (2013.01)

(58) Field of Classification Search
CPC ...... B82Y 30/00; B82Y 40/00; A61K 8/0241; A61K 8/0258; A61K 8/0262; A61K 8/0266; A61K 2800/63; A61K 8/29; A61K 8/26; A61K 2800/412; C09C 3/006; C09C 1/405; C09C 1/62; C09C 1/3669; C09C 3/10; C09C 1/3676; C09C 1/3072; C09C 1/24; C09C 1/021; C09C 1/043; C09C 1/402; A61Q 19/10; C01G 23/047; C01P 2004/64
See application file for complete search history.

(56) References Cited

U.S. PATENT DOCUMENTS

| | | |
|---|---|---|
| 3,761,418 A | 9/1973 | Kreeger et al. |
| 5,108,736 A * | 4/1992 | Schlossman .............. C09C 3/08 424/64 |
| 5,925,379 A | 7/1999 | Mandeville et al. |
| 6,083,491 A | 7/2000 | Mellul et al. |
| 6,093,447 A | 7/2000 | Johnson et al. |
| 6,132,739 A | 10/2000 | Leverett |
| 6,566,313 B1 | 5/2003 | Hohenstein et al. |
| 6,759,376 B2 | 7/2004 | Zhang et al. |
| 6,936,241 B2 | 8/2005 | Yamada et al. |
| 7,393,520 B2 | 7/2008 | Loffler et al. |
| 7,868,164 B2 | 1/2011 | Kreeger et al. |
| 2003/0068487 A1 | 4/2003 | Nguyen et al. |
| 2003/0161805 A1 | 8/2003 | Schlossman et al. |
| 2003/0179269 A1 | 9/2003 | Yamanouchi et al. |
| 2004/0122152 A1 | 6/2004 | SenGupta et al. |
| 2004/0234613 A1 | 11/2004 | Schlossman et al. |
| 2005/0031560 A9 | 2/2005 | Simonnet et al. |
| 2005/0142084 A1 | 6/2005 | Ganguly et al. |
| 2005/0169867 A1 | 8/2005 | Horino et al. |
| 2005/0220736 A1 | 10/2005 | Polonka et al. |
| 2005/0220738 A1 | 10/2005 | Patel et al. |

(Continued)

FOREIGN PATENT DOCUMENTS

| | | |
|---|---|---|
| CA | 2769908 | 3/2011 |
| CN | 1784200 | 6/2006 |

(Continued)

OTHER PUBLICATIONS

Amerchol Corporation, Apr. 2005, "SoftCAT SK Conditioning Polymers", Form No. 324-00195-0405 AMS, www.amerchol.com.

(Continued)

Primary Examiner — Hong Yu
(74) Attorney, Agent, or Firm — Hoxie & Associates LLC

(57) ABSTRACT

A composition comprising a pigment particle that is coated with a cationic material and isopropyl titanium tri-isostearate. The pigment particle can be included in a cleansing composition for deposition on a surface, such as skin.

10 Claims, No Drawings

(56) References Cited

U.S. PATENT DOCUMENTS

| | | | |
|---|---|---|---|
| 2006/0071992 A1 | 4/2006 | Sarkisian et al. | |
| 2006/0110344 A1 | 5/2006 | Hata et al. | |
| 2006/0153889 A1 | 7/2006 | Friel et al. | |
| 2006/0154072 A1 | 7/2006 | Schlossman et al. | |
| 2007/0107635 A1 | 5/2007 | Soane et al. | |
| 2007/0141002 A1 | 6/2007 | Montezinos et al. | |
| 2007/0253989 A1 | 11/2007 | Abe et al. | |
| 2009/0013481 A1* | 1/2009 | Colaco | A61Q 5/12 8/426 |
| 2009/0162408 A1 | 6/2009 | SenGupta | |
| 2009/0258807 A1 | 10/2009 | Hoffmann et al. | |
| 2010/0255044 A1 | 10/2010 | Daly et al. | |
| 2012/0145172 A1 | 6/2012 | Shao et al. | |

FOREIGN PATENT DOCUMENTS

| | | |
|---|---|---|
| CN | 101395260 A | 3/2009 |
| JP | S64-068313 A | 3/1989 |
| JP | 2004-203788 | 7/2004 |
| RU | 2351309 | 4/2009 |
| WO | WO 00/01771 | 1/2000 |
| WO | WO 00/12053 | 3/2000 |
| WO | WO 03/043567 | 5/2003 |
| WO | WO 04/100919 | 11/2004 |
| WO | WO 2004/100921 | 11/2004 |
| WO | WO 05/099651 | 10/2005 |
| WO | WO 2006/042179 | 4/2006 |
| WO | WO 2007/101586 | 9/2007 |
| WO | WO 2007/130119 | 11/2007 |
| WO | WO 2008/067186 | 6/2008 |
| WO | WO 2009/009657 | 1/2009 |

OTHER PUBLICATIONS

Faulkner et al., 1994, "Pigment Surface Treatments: A Bench Chemist's Guide," Cosmetics and Toiletries 109:69-72.
Gottschalck et al., 2008, "Polyquaternium-67", International Cosmetic Ingredient, Dictionary and Handbook, 2:2132 (abstract).
International Search Report, International Searching Authority, dated May 7, 2010, for corresponding application No. PCT/US2009/0555 1 3.
International Search Report, International Searching Authority, dated Aug. 31, 2010, for corresponding application No. PCT/US2009/0555 1 0.
Written Opinion, International Preliminary Examining Authority, dated Sep. 21, 2011, for corresponding application No. PCT/US2009/0555 1 0.
Linz, 2001, "Formulation Approaches to Interference Pignments," Allured's Cosmeics and Toiletries magazine 116(2):61-66.
Kobo Products, Inc., May 4, 2009, "Kobo Isopropyl Titanium Triisostearate (ITT), Titanate Treatment Flyer", http://www.koboproductsinc.com/I2.html.
Kobo Products, Inc., Feb. 10, 2009, "Titanate Treatment", Technical Literature ref. ITT-001, www.koboproducts.com.
Kobo Products, Inc., May 4, 2009, "Kobo Treatments, Treated Pigments & Powders", http://www.koboproductsinc.com/Treatments.html.
Merriam-Webster's Collegiate Dictionary, 2003, Entries for "composition," "particle," and "punctuation:/ slash," pp. 255, 903 and 1609.
Schlossman, Mitchell L., 1990, "Treated Pigments: New Ways to Impart Color on the Skin," Allured Publishing, Cosmetics & Toiletries magazine, pp. 53-55, 58, 60 and 62-64.
Safe Cosmetics, 2005, "Safe Cosmetics, Foundation (revised Oct. 5, 2005)", URL: www.zerozits.com/safecosmetics/foundation/html.
S.L. Jordan et al., 2007, "Effect of Hydrophobic Substitution on Cationic Conditioning Polymers"; Cosmetic Nanotechnology—Polymers and Colloids in Cosmetics, 1(2):59-71, 67, and 69.

* cited by examiner

SURFACE MODIFIED PIGMENT

This application is a Continuation of U.S. patent application Ser. No. 13/391,594 filed Feb. 21, 2012, which is claims benefit of and priority to International Application No. PCT/US2009/055513, filed Aug. 31, 2009, the contents of each of which are incorporated herein by reference in their entireties.

BACKGROUND OF THE INVENTION

There is a desire to increase the radiance of skin in such a way that consumers can perceive their skin being radiant, glossy, and/or shiny. These attributes are evaluated via consumer assessment. Skin radiance is also correlated to skin gloss measurements. While radiance can be imparted to skin by using a leave on product that deposits a pigment that can increase gloss, it would be desirable to be able to increase gloss by using a cleansing composition that includes a pigment.

The problem with using a cleansing composition is that the composition performs its function of cleaning by removing oil and dirt from skin. To be effective, the pigment needs to be modified to adhere to skin to avoid being washed away by the cleansing composition.

It is desirable to create a pigment that can adhere to skin that can be delivered from a cleansing composition.

SUMMARY OF THE INVENTION

A composition comprising a pigment particle that is coated with a cationic material and isopropyl titanium triisostearate. Also a method of increasing gloss on a substrate comprising applying the composition to the substrate.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight The amounts given are based on the active weight of the material.

The invention relates to a pigment particle that is coated with cationic material and isopropyl titanium triisostearate.

The pigment particle can be any particle that imparts gloss. Examples of pigment particles include, but are not limited to, mica/titanium dioxide, mica/iron oxide, mica, titanium dioxide, zinc oxides, iron oxides, chromium oxides, silica, talc, kaolin, and compositions thereof. In one embodiment, the pigment particle is mica/titanium dioxide. The particle size can be chosen to be any size that provides a measurable gloss. The particle size of the particle is the size before coating with the cationic material or any other coating. In one embodiment, the particle size is 1 to 1000 microns. In other embodiments, the particle size is at least 10, 20, 30, 40, 50, 60, 60, 80, 90, 100, or 150 microns. In other embodiments, the particle size is up to 100, 150, 250, 300, 350, 400, 450, 500, 600, 700, 800, 900, or 1000 microns. Any of the preceding minimum amounts can be combined with any of the maximum amounts to form a range. In one embodiment, the particle size is 50 to 100 microns.

The cationic material can be any material with a cationic charge. In some embodiments, the cationic material is a cationic material selected from the INCI Quaternium series. In some embodiments, the cationic material is a cationic polymer. In certain embodiments, the cationic material is selected from the INCI Polyquaternium series. Examples of Polyquaternium and Quaternium series materials include, but are not limited to, Polyquaternium-1, Polyquaternium-2, Polyquaternium-4, Polyquaternium-5 Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-42, Polyquaternium-43, Polyquaternium-44, Polyquaternium-45, Polyquaternium-46, Polyquaternium-47, Polyquaternium-48, Polyquaternium-49, Polyquaternium-50, Polyquaternium-51, Polyquaternium-52, Polyquaternium-53, Polyquaternium-54, Polyquaternium-55, Polyquaternium-56, Polyquaternium-57, Polyquaternium-58, Polyquaternium-59, Polyquaternium-60, Polyquaternium-61, Polyquaternium-62, Polyquaternium-63, Polyquaternium-64, Polyquaternium-65, Polyquaternium-66, Polyquaternium-67, Polyquaternium-68, Polyquaternium-69, Polyquaternium-70, Polyquaternium-71, Polyquaternium-72, Polyquaternium-73, Polyquaternium-74, Polyquaternium-75, Polyquaternium-76, Polyquaternium-77, Polyquaternium-78, Polyquaternium-79, Polyquaternium-80, Polyquaternium-81, Polyquaternium-82, Polyquaternium-83, Polyquaternium-84, Polyquaternium-85, Polyquaternium-86 Polyquaternium-87, Polyquaternium-88, Polyquaternium-90, Polyquaternium-93, Polyquaternium-94, Polyquaternium-4/Hydroxypropyl Starch Copolymer, Quaternium-8, Quaternium-14, Quaternium-15, Quaternium-16, Quaternium-18, Quaternium-18 Bentonite, Quaternium-18/Benzalkonium Bentonite, Quaternium-18 Hectorite, Quaternium-18 Methosulfate, Quaternium-22, Quaternium-24, Quaternium-26, Quaternium-27, Quaternium-30, Quaternium-33, Quaternium-43, Quaternium-45, Quaternium-51, Quaternium-52, Quaternium-53, Quaternium-56, Quaternium-60, Quaternium-61, Quaternium-63, Quaternium-70, Quaternium-71, Quaternium-72, Quaternium-73, Quaternium-75, Quaternium-76 Hydrolyzed Collagen, Quaternium-77, Quaternium-78, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein, Quaternium-80, Quaternium-81, Quaternium-82, Quaternium-83, Quaternium-84, Quaternium-85, Quaternium-86, Quaternium-87, Quaternium-88, Quaternium-89, Quaternium-90, Quaternium-90 Bentonite, Quaternium-91, Quaternium-92, Quaternium-93, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Silicone Quaternium-22, Silicone Quaternium-24, PEG-2 Cocoyl Quaternium-4, PEG-15 Cocoyl Quaternium-4, PEG-2 Oleyl Quaternium-4, PEG-15 Oleyl Quaternium-4, PEG-2 Stearyl Quaternium-4, PEG-15 Stearyl Quaternium-4, Polydimethylaminopropyl Methacrylamide Methylchloride Quaternium.

In one embodiment, the cationic material is Polyquaternium-67, which is the generic INCI name for a polymeric quaternary ammonium salt of hydroxyethyl cellulose reacted with a trimethyl ammonium substituted epoxide and a lauryl dimethyl ammonium (dimethyldodecyl) substituted epoxide. Polyquaternium-67 is available from the Amerchol subsidiary of Dow Chemical Company under the SoftCAT trade name. In one embodiment, the Polyquarternium-67 is SoftCAT SK-MH.

In other embodiments. the cationic material is a cationic polymer. In the present application, the expression "cationic polymer" designates a polymer containing cationic groups or groups which can be ionized into cationic groups. In certain embodiments, cationic polymers are chosen from those containing units comprising primary, secondary, tertiary and/or quaternary amine groups which may either form part of the polymer chain or be carried by a side substituent. In certain embodiments, the cationic polymers have a molecular mass of between $10^3$ and $3\times10^6$. In certain embodiments, the cationic polymers used are those containing at least 10% by weight of units comprising amine groups or quaternary ammonium groups whose quaternization value, expressed as cationic equivalent per gram of polymer, is for example at least equal to 0.05 cationic meq/g (meq: milliequivalent). When the cationic polymer carries amine or quaternary ammonium groups carried by a side substituent, the polymer chain is for example an acrylic, vinyl, siliconized, fluorinated or saccharide chain. In certain embodiments, the cationic polymers are selected from quaternized proteins, quaternized polysiloxanes, polyamine type polymers, polyaminoamide and quaternary polyammonium.

The quaternized proteins are in particular chemically modified polypeptides carrying at the chain end, or grafted thereto, quaternary ammonium groups. Among these proteins, there may be mentioned especially:
hydrolysates of collagen carrying triethylammonium groups such as the products sold under the name QUAT-PRO E™ by the company Maybrook and termed in the CTFA dictionary "Triethonium Hydrolyzed Collagen Ethosulfate", hydrolysates of collagen carrying trimethylammonium or trimethylstearylammonium chloride groups, sold under the name QUAT-PRO S™ by the company Maybrook and termed in the CTFA dictionary "Steartrimonium Hydrolyzed Collagen";

hydrolysates of animal proteins carrying trimethylbenzylammonium groups such as the products sold under the name CROTEIN BTA™ by the company Croda and termed in the CTFA dictionary "Benzyltrimonium hydrolyzed animal protein";

hydrolysates of proteins carrying on the polypeptide chain quaternary ammonium groups comprising at least one alkyl radical having 1 to 18 carbon atoms.

Among these protein hydrolysates, there may be mentioned inter alia:

CROQUAT L™ whose peptide chain has a mean molecular weight of about 2,500 and whose quaternary ammonium group comprises a $C_{12}$ alkyl group;

CROQUAT M™ whose peptide chain has a mean molecular weight of about 2,500 and whose quaternary ammonium group comprises a $C_{10}$-$C_{18}$ alkyl group;

CROQUAT S™ whose polypeptide chain has a mean molecular weight of about 2,700 and whose quaternary ammonium group comprises a $C_{18}$ alkyl group;

CROTEIN Q™ whose polypeptide chain has a mean molecular weight of the order of 12,000 and whose quaternary ammonium group comprises at least one alkyl group having 1 to 18 carbon atoms. These different products are sold by the company Croda.

Other quaternized proteins are those corresponding to the formula:

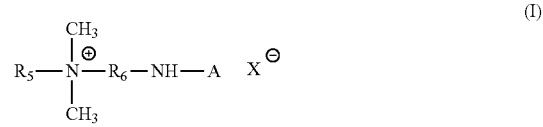

(I)

X⁻ is an anion of an organic or inorganic acid in which A designates a protein residue derived from hydrolysates of collagen protein, $R_5$ designates a lipophilic group comprising up to 30 carbon atoms, $R_6$ represents an alkylene group having 1 to 6 carbon atoms, these proteins have a molecular weight of between 1,500 and 10,000, preferably 2,000 and 5,000. There may be mentioned for example the products sold by the company Inolex, under the name LEXEIN QX 3000™, termed in the CTFA dictionary "Coco-trimonium Collagen Hydrolysate".

Among the quaternized proteins, there may also be mentioned quaternized plant proteins, such as wheat, maize or soya bean proteins; as quaternized wheat proteins, there may be mentioned those marketed by the company CRODA under the names HYDROTRITICUM WQ or QM™, termed in the CTFA dictionary "cocodimonium hydrolysed wheat protein", HYDROTRITICUM QL™ termed in the CTFA dictionary "Laurdimonium hydrolysed wheat protein", or alternatively under the name HYDROTRITICUM QS™ termed in the CTFA dictionary "Steardimonium hydrolysed wheat protein".

Another family of cationic polymers are the siliconized cationic polymers. Among these polymers, there may be mentioned (a) the quaternized polysiloxanes termed in the CTFA dictionary "Amodimethicone" and corresponding to the formula:

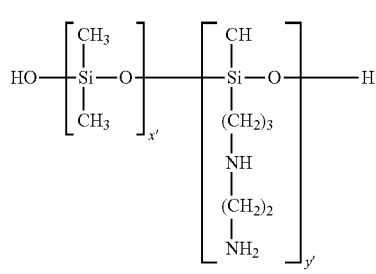

(II)

in which x' and y' are integers depending on the molecular weight which is generally between 5,000 and 10,000;
(b) the siliconized cationic polymers corresponding to the formula:

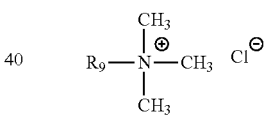

(III)

in which
G is a hydrogen atom or a phenyl or OH group or a $C_1$-$C_8$ alkyl, preferably methyl, group, a designates 0 or an integer from 1 to 3, and preferably 0,
b designates 0 or 1 and preferably 1,
the sum (n+m) is an integer from 1 to 2,000 and preferably from 50 to 150, it being possible for n to designate a number from 0 to 1,999 and preferably from 49 to 149 and it being possible for m to designate an integer from 1 to 2,000 and preferably from 1 to 10;
R' is a monovalent radical of formula $C_qH_{2q}L$ in which q is a number from 2 to 8 and L is chosen from the groups:
NR"—$CH_2$—$CH_2$—N(R")$_2$
N(R")$_2$
$^\oplus$N($R^{40}$)$_3$$A^\oplus$
$^\oplus$N(R")H$_2$$A^\ominus$
NR"$CH_2$—$CH_2$—$^\oplus$NR"H$_2$$A^\ominus$;
NR"$CH_2$—$CH_2$—$^\oplus$NR"H$_2$$A^\ominus$ in which R" may designate hydrogen, phenyl, benzyl, a monovalent saturated hydrocarbon radical and preferably an alkyl radical having from 1 to 20 carbon atoms and $A^\ominus$ represents a halide ion such as fluoride, chloride, bromide or iodide.

A particularly useful product entering into this definition is the polymer termed "trimethylsilylamodimethicone" corresponding to the formula:

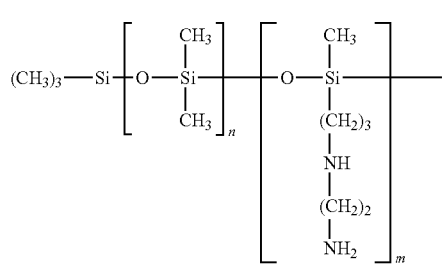

(IV)

in which n and m have the meanings given above (of formula III). Such polymers are described in Patent Application EP-A-95238.
(c) the siliconized cationic polymers corresponding to the formula:

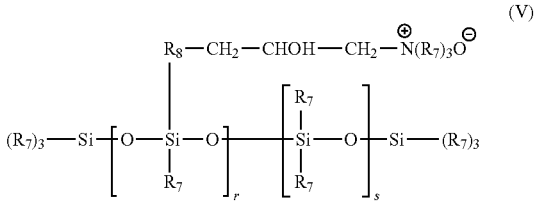

(V)

in which
$R^7$ designates a monovalent hydrocarbon radical having from 1 to 18 carbon atoms and in particular an alkyl or alkenyl and, preferably, methyl radical;
$R_8$ designates a divalent hydrocarbon radical, preferably a $C_1$-$C_{18}$ alkylene radical or a $C_1$-$C_{18}$ and preferably $C_1$-$C_8$ divalent alkylenoxy radical;
$Q^-$ is a halide, preferably chloride, ion;
r represents a mean statistical value from 2 to 20 and preferably from 2 to 8;
s represents a mean statistical value from 20 to 200 and preferably from 20 to 50. Such polymers are described more particularly in U.S. Pat. No. 4,185,087. A polymer entering into this class is the polymer sold by the company Union Carbide under the name UCAR SILICONE ALE 56™.

When these siliconized polymers are used, a particularly advantageous embodiment is their simultaneous use with cationic surface-active agents, optionally non-ionic surface-active agents. There may be used for example in the compositions conforming to the invention the commercial product sold under the name EMULSION CATIONIQUE DC 929™ by the company DOW CORNING which comprises, in addition to amodimethicone, a cationic surface-active agent corresponding to the formula:

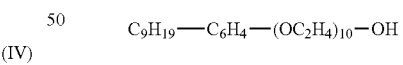

in which $R_9$ designates a mixture of alkenyl and/or alkyl radicals having from 14 to 22 carbon atoms, derived from tallow fatty acids, and a non-ionic surface-active agent of formula:

$C_9H_{19}$—$C_6H_4$—$(OC_2H_4)_{10}$—OH known under the name NONOXYNOL 10™.

Another composition which can be used in this embodiment of the invention is the composition containing the product sold under the name DOW CORNING Q2 7224™ by the company Dow Corning comprising in combination the trimethylsilylamodimethicone of formula (IV), a non-ionic surface-active agent of formula:

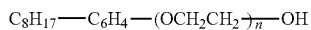

also termed octoxynol-40, another non-ionic surface-active agent of formula:

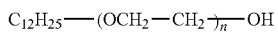

where n=6 also termed isolaureth-6, and glycol.

The polyamine, polyaminoamide and quaternary polyammonium type polymers which can be used in conformity with the present invention are described in particular in French Patent nos. 8207996 or 8404475. Among these polymers, there may be mentioned:

(1) the quaternized or non-quaternized vinylpyrrolidone-dialkylaminoalkyl acrylate or methacrylate copolymers such as the products sold under the name (GAFQUAT™ by the company GAP CORPORATION such as for example GAFQUAT 734™ or 755™ or alternatively the product termed COPOLYMERE 937™. These polymers are described in detail in French Patents 2,077,143 and 2,393,573.

(2) The cellulose ether derivatives comprising quaternary ammonium groups described in French Patent 1,492,597 and in particular the polymers marketed under the names "JR" (JR 400™, JR 125™, JR 30M™) or "LR" (LR 400™, LR 30 M™) by the company Union Carbide Corporation. These polymers are also defined in the CTFA dictionary as quaternary ammonium salts of hydroxyethyl cellulose having reacted with an. epoxide substituted by a trimethylammonium group.

(3) The cationic cellulose derivatives such as the cellulose copolymers or the cellulose derivatives grafted with a water-soluble quaternary ammonium monomer and which are described in greater detail in U.S. Pat. No. 4,131,576 such as hydroxyalkyl celluloses like hydroxymethyl, hydroxyethyl or hydroxypropyl celluloses grafted with a salt of methacryloylethyl, trimethylammonium, methacrylamidopropyl trimethylammonium or dimethyldiallylammonium. The commercial products corresponding to this definition are more particularly the products sold under the name CELQUAT L 200™ and CELQUAT H 100™ by the company National Starch.

(4) The cationic polysaccharides described more particularly in U.S. Pat. Nos. 3,589,578 and 4,031,307 and more particularly the product marketed under the name JAGUAR C. 13 S™ sold by the company Meyhall.

(5) The polymers consisting of piperazinyl units and straight or branched chain divalent alkylene or hydroxyalkylene radicals, optionally interrupted by oxygen, sulphur or nitrogen atoms or by aromatic or heterocyclic rings as well as the oxidation and/or quaternization products of these polymers. Such polymers are described in French Patents 2,162,025 and 2,280,361.

(6) The water-soluble polyaminopolyamides prepared in particular by polycondensation of an acidic compound with a polyamine. These polyaminoamides may be cross-linked by an epihalohydrin, a diepoxide, a dianhydride, an unsaturated anhydride, a bis-unsaturated derivative, a bis-halohydrin, a bis-azetidinium, a bis-haloacyldiamine, a bis-alkyl halide or alternatively by an oligomer resulting from the reaction of a bifunctional compound reactive towards a bis-halohydrin, a bis-azetidinium, a bis-haloacyldiamine, a bis-alkyl halide, an epihalohydrin, a diepoxide or a bis-unsaturated derivative; the cross-linking agent being used especially in proportions ranging from 0.025 to 0.35 mole per amine group of the polyaminopolyamide. These polyaminopolyamides may be alkylated or if they comprise one or more quaternized tertiary amine functional groups. Such polymers are described in particular in French Patents 2,252,840 and 2,368,508.

(7) The polyaminopolyamide derivatives resulting from the condensation of polyalkylene polyamines with polycarboxylic acids followed by an alkylation using bifunctional agents. There may be mentioned for example the adipic acid-dialkylaminohydroxyalkyldialkylenetriamine polymers in which the alkyl radical comprises 1 to 4 carbon atoms and preferably designates methyl, ethyl, or propyl. Such polymers are described in French Patent 1,583,363. Among these derivatives, there may be mentioned more particularly the adipic acid/dimethylaminohydroxypropyl/ diethylenetriamine polymers sold under the names CARTARETINE F, $F_4$ or $F_8$™ by the company Sandoz.

(8) The polymers obtained by reaction of a polyalkylenepolyamine comprising two primary amine groups and at least one secondary amine group with a dicarboxylic acid chosen from diglycolic acid, and saturated aliphatic dicarboxylic acids having 3 to 8 carbon atoms. The mole ratio between the polyalkylenepolyamine and the dicarboxylic acid being between 0.8:1 and 1.4:1; the resulting polyaminopolyamide being reacted with epichlorohydrin in a mole ratio of epichlorohydrin to the secondary amine group of the polyaminopolyamide of between 0.5:1 and 1.8:1. Such polymers are described in particular in U.S. Pat. Nos. 3,227,615 and 2,961,347.

Polymers of this type are in particular marketed under the name HERCOSETT 57™ by the company Hercules Incorporated or alternatively under the name PD 170™ or DELSETTE 101™ by the company Hercules in the case of the adipic acid/epoxypropyl/diethylenetriamine copolymer.

(9) The cyclopolymers having a molecular weight of 20,000 to 3,000,000 such as homopolymers comprising as principal constituent of the chain units corresponding to the formula (VI) or (VI')

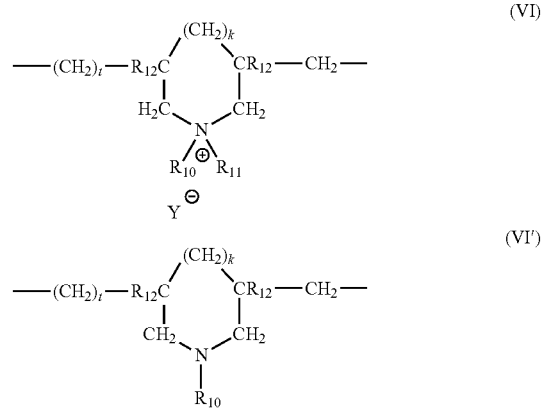

k and t are equal to 0 or 1, and the sum of k+t–1, $R_{12}$ designates hydrogen or methyl, $R_{10}$ and R11 designate independently of each other an alkyl group having from 1 to 22 carbon atoms, a hydroxyalkyl group in which the alkyl group preferably has 1 to 5 carbon atoms, a lower amidoalkyl group and where $R_{10}$ and $R_1$ may designate together with the nitrogen atom to which they are attached heterocyclic groups such as piperidyl or morpholinyl, as well as the copolymers comprising the units of formula (VI) or (VI') and units derived from acrylamide or diacetone acrylamide, $Y^\ominus$ is an anion such as bromide, chloride, acetate, borate, citrate, tartrate, bisulphate, bisulphite, sulphate and phosphate. Among the polymers defined above, there may be mentioned more particularly the dimethyldiallylammonium chloride homopolymer sold under the name MERQUAT 100™ having a molecular weight of less than 100,000 and the dimethyldiallylammonium chloride and acrylamide copolymer having a molecular weight greater than 500,00 and sold under the name MERQUAT 550™ by the company Merck. These polymers are described more particularly in French Patent 2,080,759 and its certificate of addition no. 2,190,406.

(10) The quaternary polyammonium polymer containing recurring units corresponding to the formula:

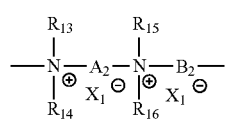
(VII)

in which $R_{13}$ and $R_{14}$, $R_{15}$ and $R_{16}$ being identical or different, represent aliphatic, alicyclic or arylaliphatic radicals containing from 1 to 20 carbon atoms or low hydroxyalkylaliphatic radicals, or alternatively $R_{13}$ and $R_{14}$ and $R_{15}$ and $R_{16}$, together or separately, constitute with the nitrogen atoms to which they are attached, heterocycles optionally containing a second heteroatom other than nitrogen or alternatively $R_{13}$, $R_{14}$, $R_{15}$ and $R_{16}$ represent a linear or branched $C_2$-$C_6$ alkyl radical substituted by a nitrile, ester, acyl or amide group or a group

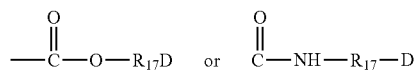

where $R_{17}$ is an alkylene and D a quaternary ammonium group.

$A_2$ and $B_2$ represent polymethylene groups containing from 2 to 20 carbon atoms which may be linear or branched, saturated or unsaturated and which may contain, bonded to or intercalated into the principal chain, one or more aromatic rings, or one or more oxygen or sulphur atoms or SO, $SO_2$, disulphide, amino, alkylamino, hydroxyl, quaternary ammonium, ureido, amide or ester groups and $X^e_i$ designates an anion derived from an inorganic or organic acid.

$A_2$ and $R_{13}$ and $R_{15}$ may form with the two nitrogen atoms to which they are attached, a piperazine ring; in addition, if $A_2$ designates a saturated or unsaturated, linear or branched alkylene of hydroxyalkylene radical, $B_2$ may also designate a group:

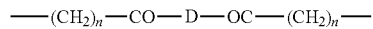

in which D designates:
a) a glycol residue of formula: O—Z—O—
where Z designates a linear or branched hydrocarbon radical or a group corresponding to the formula:

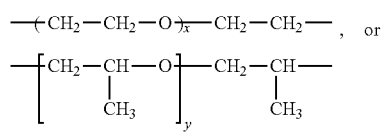

where x and y designate an integer from 1 to 4, representing a defined and unique degree of polymerization or any number from 1 to 4 representing a mean degree of polymerization;

b) a bis-secondary diamine residue such as a piperazine derivative, c) a bis-primary diamine residue formula: —NH—Y—NH—, where Y designates a linear or branched hydrocarbon radical or alternatively the bivalent radical d) a ureylene group of formula: —NH—CO—NH—;

$X^\ominus$ is an anion such as chloride or bromide.

These polymers have a molecular mass generally between 1,000 and 100,000. Polymers of this type are described in particular in French Patents 2,320,330, 2,270,846, 2,316, 271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,653, 4,026,945 and 4,027,020.

(11) The quaternary polyammonium polymers consisting of the units of formula:

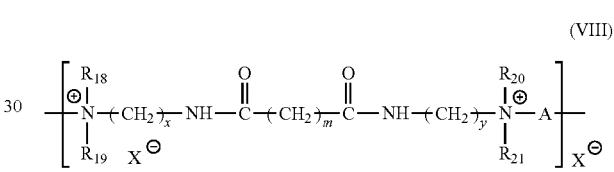
(VIII)

in which $R_{18}$, $R_{19}$, $R_{20}$ and $R_{21}$ which are identical or different, represent a hydrogen atom or a methyl, ethyl, propyl .beta.-hydroxyethyl, .beta.-hydroxypropyl or —$CH_2CH_2(OCH_2CH_2)_p$OH radical where p is equal to 0 or an integer between 1 and 6, provided that $R_{18}$, $R_{19}$, $R_{20}$ and $R_{21}$ do not simultaneously represent a hydrogen atom, x and y, which are identical or different, are integers between 1 and 6;

m is equal to 0 or an integer between 1 and 34,

X designates a halogen atom,

A designates the residue of a dihalide radical and preferably represents —$CH_2$—$CH_2$—O—$CH_2$—$CH_2$—. Such compounds are described in greater detail in European Patent Application 122 324.

(12) The homopolymers or copolymers derived from acrylic or methacrylic acids comprising the units:

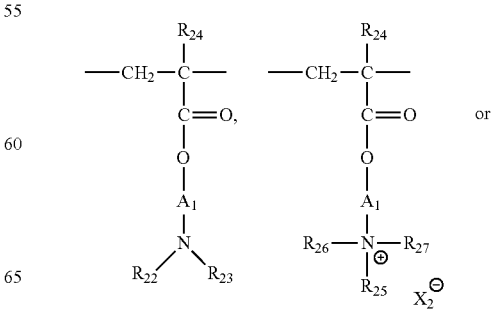

-continued

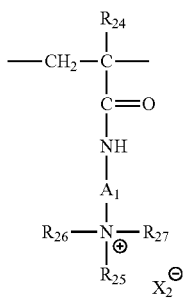

in which $R_{24}$ designates H or $CH_3$. $A_1$ is a linear or branched alkyl group of 1 to 6 carbon atoms, or a hydroxyalkyl group of 1 to 4 carbon atoms, $R_{25}$, $R_{26}$, $R_{27}$, which are identical or different, represent an alkyl group having from 1 to 18 carbon atoms of a benzyl radical, $R_{22}$ and $R_{23}$ represent hydrogen or an alkyl group having from 1 to 6 carbon atoms. $X_2^{\ominus}$ designates a methosulphate anion or a halide such as chloride or bromide. The comonomer(s) which can be used belongs(belong) to the family comprising: acrylamide, methacrylamide, diacetone acrylamide, acrylamide and methacrylamide which are nitrogen-substituted by lower alkyls, alkyl esters of acrylic of methacrylic acids, vinylpyrrolidone and vinyl esters.

13) The quaternary vinylpyrrolidone and vinylimidazole polymers such as for example the products marketed under the names LUVIQUAT FC 905™, FC 550™ and FC 370.degree. by the company BASF.

Other cationic polymers which can be used in conformity with the invention are polyalkyleneimines, in particular polyethyleneimines, polymers containing vinylpyridine or vinylpyridinium units, condensates of polyamines and epichlorohydrin, quaternary polyureylenes and chitin derivatives.

Among the cationic polymers which can be used in the compositions of the invention, there may be mentioned especially the following polymers: the polymer comprising the units of formula:

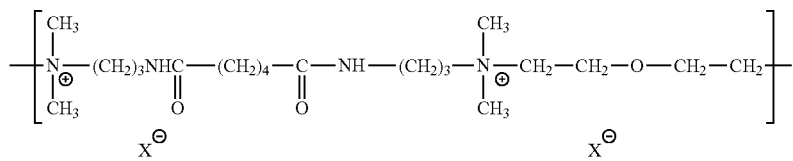

sold under the name MIRAPOL AD 1™ by the company Miranol, the polymer comprising the units of formula:

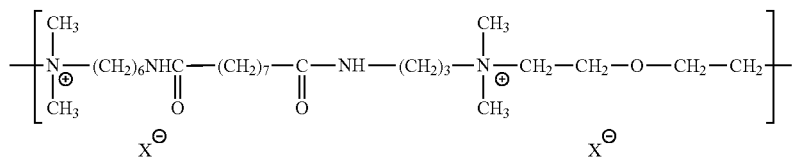

sold under the name MIRAPOL AZ1™ by the company Miranol, poly(methacrylamidopropyltrimethylammonium chloride) sold under the name POLYMAPTAC™ by the company Texaco Chemicals;

a quaternized polymer of the ionene type described in French Patent no. 2,270,846 and more particularly those comprising the units:

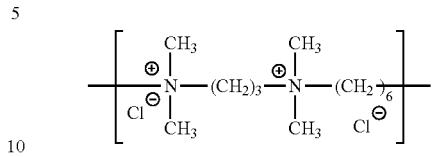

the dimethyldiallylammonium cyclopolymers sold under the names MERQUAT 100T™ and MERQUAT 550™ by the company Merck;

the quaternary vinylpyrrolidone and vinylimidazole polymers such as those sold under the names LUVIQUAT FC 905™, FC 550™ and FC 370™ by the company BASF the quaternized or non-quaternized vinylpyrrolidone/dialkylaminoalkyl acrylate or methacrylate copolymers such as the products sold under the names COPOLYMERE 937™, GAFQUAT 734™ or 755™ by the company GAF;

the quaternary cellulose ether polymers such as those sold under the names "JR" such as for example JR 125™, JR 400™, JR 30-M™ and LR such as LR 400™ and LR 30™ by the company Union Carbide Corporation;

the cationic cellulose derivatives such as the products sold under the names CELQUAT L 200™ and CALQUAT H 100™ by the company National Starch;

the quaternary ammonium polymers of the type described in the U.S. Pat. No. 4,157,388 and more particularly the polymer comprising units of formula:

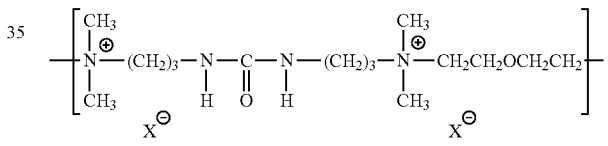

sold under the name MIRAPOL A 15™ by the company Miranol; poly(dimethylbutenylammonium chloride)-.alpha.,.omega.-bis(triethanolammonium chloride) sold under the

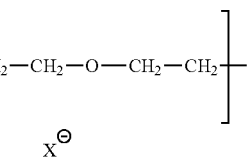

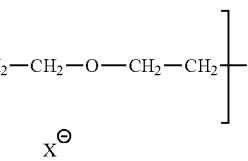

name ONAMER M™ by the company Onyx Internationale; the amine-containing polymers with siliconized skeleton such as then amodimethicone contained in the cationic emulsion DC929™ marketed by Dow Corning.

In one embodiment, the amount of cationic material on the total weight of the pigment particle is 0.1 to 10 weight %. In other embodiments the amount of cationic material is at least 0.1, 0.2, 0.3, 0.4, 0.5, 0.6, 0.7, 0.8, 0.9, 1, 1.5, 2, 2.5, 3, 3.5, 4, 4.5, or 5 weight %. In other embodiments, the amount of cationic material is less than 1, 1.5, 2, 2.5, 3, 3.5, 4, 4.5, 5, 6, 7, 8, 9, or 10 weight %. Any of the preceding minimum amounts can be combined with any of the maximum amounts to form a range. In another embodiment, the pigment particle has a size of 50 to 100 microns, and the amount of cationic material on these particles can be any of the preceding amounts.

The pigment particle also includes isopropyl titanium triisostearate (ITT). The isopropyl titanium triisostearate can be added to the pigment particle before or after the cationic material is applied to the pigment particle. In one embodiment, the amount of ITT on the total weight of the pigment particle is 0.1 to 5 weight %. In other embodiments, the amount of ITT is at least 0.1, 0.5, 1, 1.5, 2, 2.5, 3, 3.5, 4, or 4.5 weight %. In other embodiments, the amount of ITT is less than 1, 2, 3, 4 or 5 weight %. Any of the preceding minimum amounts can be combined with any of the maximum amounts to form a range. In another embodiment, the pigment particle has a particle size of 50 to 100 microns, and the amount of ITT on these particles can be any of the preceding amounts.

In one embodiment, the pigment particle is pre-coated. By pre-coated, it is meant that the pigment particle is coated with the cationic material prior and the isopropyl titanium triisostearate to the pigment particle being added to a composition that contains material in addition to itself.

A particle with the cationic material that includes the ITT added after the cationic material is applied can be made using the following procedure.

(i) The cationic material is added under mixing to water in a vessel in which there is a sufficient amount of the water to dissolve the cationic material under heating.
(ii) The cationic material/water is heated and mixed until the cationic material is dissolved.
(iii) Pigment is mixed into the mixture.
(iv) The mixture is dried at 105° C. until sufficiently dry (approximately 3 hours).
(v) The material is cooled and chopped gently.
(vi) The material is sieved (for example in a No. 40 sieve) to remove agglomerate.
(vii) Isopropyl titanium triisostearate is dissolved in ISOPAR C solvent in a ratio of 1:2.
(viii) The solution is added to the powder obtained in step (ix) under mixing in a blender.
(ix) The solution is dried at 85° C. for 1 hour.
(x) The material is cooled and chopped gently.

A particle with the cationic material that includes the ITT added before the cationic material is applied can be made using the following procedure.

(i) Isopropyl titanium triisostearate is dissolved in ISOPAR C solvent in a ratio of 1:2.
(ii) The solution is added to pigment particles under mixing in a blender.
(iii) The solution is dried at 85° C. for 1 hour.
(iv) The material is cooled and chopped gently.
(v) The cationic material is added under mixing to water in a vessel in which there is a sufficient amount of the water to dissolve the cationic material under heating.
(vi) The cationic material/water is heated and mixed until the cationic material is dissolved.
(vii) Pigment from step (iv) is mixed into the mixture.
(viii) The mixture is dried at 105° C. until sufficiently dry (approximately 3 hours).
(ix) The material is cooled and chopped gently.
(xi) The material is sieved (for example in a No. 40 sieve) to remove agglomerate.

The pigment particle can be included in a cleansing composition, such as a body wash, shower gel, liquid hand soap, or bar soap. The amount of the particle in the cleansing system can be any amount that is generally used for particles. In certain embodiments, the amount is 0.01 to 20 weight % of the composition, 0.1 to 10 weight %, or 0.15 to 2 weight %. In other embodiments, the amount is at least 0.1, 0.15, 0.2, 0.3, 0.4, 0.5, 0.6, 0.7, 0.8, 0.9, 1, 1.2, 1.2, 1.3, 1.4, 1.5, or 2 weight % up to 20 weight %. The particle can be added to the cleansing composition by any standard addition procedure for adding pigments.

A variety of anionic surfactants can be utilized in a cleansing composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates, Stepan-Mild™ PCL sodium methyl-2 sulfolaurate and disodium 2-sulfolaurate and sodium lauryl sulfoacetate blend, and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pareth sulfate, and combinations thereof. Anionic surfactants can be included in any desired amount. In one embodiment, anionic surfactants are present in the composition in an amount of 0 to about 15% by weight. In one embodiment, anionic surfactants are present in an amount of about 6 to about 8% by weight.

Amphoteric surfactants may also be included in the composition. These surfactants are typically characterized by a combination of high surfactant activity, lather forming and mildness. Amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g. carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxylmethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, strearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as those that include an amido groups such as the cocamidopropyl and cocoamidoethyl betaines.

Amphoteric surfactants can be included in any desired amount. In one embodiment, amphoteric surfactants are present in the composition in an amount of 0 to about 15% by weight. In one embodiment, the amphoteric surfactants are present in the composition in an amount of about 4 to about 6% by weight.

Examples of nonionic surfactants include, but are not limited to, polysorabate 20, long chain alkyl glucosides having $C_8$-$C_{22}$ alkyl groups; coconut fatty acid monoethanolamides such as cocamide MEA; coconut fatty acid diethanomides, fatty alcohol ethoxylates (alkylpolyethylene glycols); alkylphenol polyethylene glycols; alkyl mercaptan polyethylene glycols; fatty amine ethoxylates (alkylaminopolyethylene gylcols); fatty acid ethoxylates (acylpolyethelene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof. Nonionic surfactants can be included in any desired amount. In one embodiment, nonionic surfactants are present in the composition in an amount of 0 to about 3% by weight. In one embodiment, nonionic surfactants are present in the composition in an amount of about 0.5 to about 1.5% by weight.

Cationic surfactants can also be included in the composition. Examples of cationic surfactants include, but are not limited to any quaternium or polyquaternium compound. Cationic surfactants can be included at any desired level. In one embodiment, cationic surfactants are present in the composition in an amount of 0 to about 2% by weight. In one embodiment, cationic surfactants are present in the composition in an amount of about 0.1 to about 0.3% by weight.

Many additional surfactants are described in McCUTCHEON'S DETERGENTS AND EMULSIFIERS (1989) and other reference materials that are well known to those of ordinary skill in the art.

Additionally, a suspending agent can be included to structure the surfactant to aid in suspending particles. Suspending agents are any material that increases the ability of the composition to suspend material. Examples of suspending agents include, but are not limited to, synthetic structuring agents, polymeric gums, polysaccharides, pectin, alginate, arabinogalactan, carrageen, gellan gum, xanthum gum, guar gum, rhamsan gum, furcellaran gum, and other natural gum. A synthetic structuring agent in one embodiment is a polyacrylate. One acrylate aqueous solution used to form a stable suspension of the solid particles is manufactured by Lubrizol as CARBOPOL™ resins, also known as CARBOMER™, which are hydrophilic high molecular weight, crosslinked acrylic acid polymers. In one embodiment, the polymer is CARBOPOL™ Aqua SF-1. Other polymers that can be used include, but are not limited to, CARBOPOL™ Aqua 30, CARBOPOL™ 940 with a molecular weight of approximately 4,000,000 and CARBOPOL™ 934 with a molecular weight of approximately 3,000,000.

The suspending agents can be used alone or in combination. The amount of suspending agent can be any amount that provides for a desired level of suspending ability. In one embodiment, the suspending agent is present in an amount of about 0.01 to about 15% by weight of the composition. In other embodiments, the amount of suspending agent is about 1% to about 10%.

The cleansing composition can contain an oil and/or petrolatum. Oils that can be used can be any vegetable oil, such as sunflower, soybean, castor, etc.

The pigment particle can also be included in an oral care composition for delivery of the pigment particle to a surface in the oral cavity, such as teeth.

The pigment particle can also be included in a home care composition, such as hard surface cleaner, a dishwashing composition, a fabric softener, or a laundry detergent.

The composition can be used in a method to increase the gloss on a substrate. The composition is applied to the substrate. The particle that is used is a particle that can provide gloss. After applying, the composition can be left for a period of time and then removed. The period of time can be any desired time period, such as 5, 10, 15, 20, 30, 45, or 60 seconds, or 1, 2, 3, 4, 5, 10, 15, 30, 60 minutes, or any length of time.

The applying can be from a cleansing composition in which the composition is applied to skin to wash the skin. After applying and lathering the composition on skin, the composition can be left for a period of time on skin before the lather is rinsed and the skin is dried.

What is claimed is:

1. A method for preparing a body wash, shower gel, liquid hand soap or bar soap composition comprising a pigment particle pre-coated with Polyquaternium-67 and isopropyl titanium triisostearate, the method comprising the steps of:
    (a) preparing a pigment particle coated with Polyquaternium-67 and isopropyl titanium triisostearate, by:
        (i) dissolving the Polyquaternium-67 in water in a vessel to form a mixture;
        (ii) adding the pigment particle to the mixture in step (i);
        (iii) drying the mixture from step (ii);
        (iv) cooling the dried mixture;
        (v) sieving the mixture from step (iv) to remove agglomerate thereby producing a sieved powder;
        (vi) adding to the sieved powder a solution of isopropyl titanium triisostearate dissolved in a solvent;
        (vii) mixing or blending the solution from step (vi), and
        (viii) drying the mixed or blended solution to produce the coated pigment particle; and
    (b) combining the coated pigment particle with one or more components of the body wash, shower gel, liquid hand soap or bar soap selected from anionic surfactants, amphoteric surfactants, nonionic surfactants, suspending agents, oil and petrolatum.

2. The method of claim 1, wherein the dissolving in step (i) is accomplished with heating.

3. The method of claim 1, wherein the drying in step (iii) is performed by heating.

4. The method of claim 3, wherein the heating is at approximately 105° C. for approximately 3 hours.

5. The method of claim 1, wherein step (iv) further comprises gently chopping the dried mixture.

6. The method of claim 1, wherein the sieving in step (v) comprises sieving with a No. 40 sieve.

7. The method of claim 1, wherein step (viii) comprises heating the mixed or blended solution.

8. The method of claim 1, wherein step (viii) comprises heating the mixed or blended solution at approximately 85° C. for 1 hour.

9. The method of claim 8, wherein step (viii) further comprises cooling the mixed or blended solution and gently chopping the cooled product.

10. The method of claim 1, wherein the particle is mica/titanium dioxide.

* * * * *